Oct. 11, 1966 E. ASJES, JR Plant Pat. 2,678
ASH TREE
Filed Feb. 23, 1965
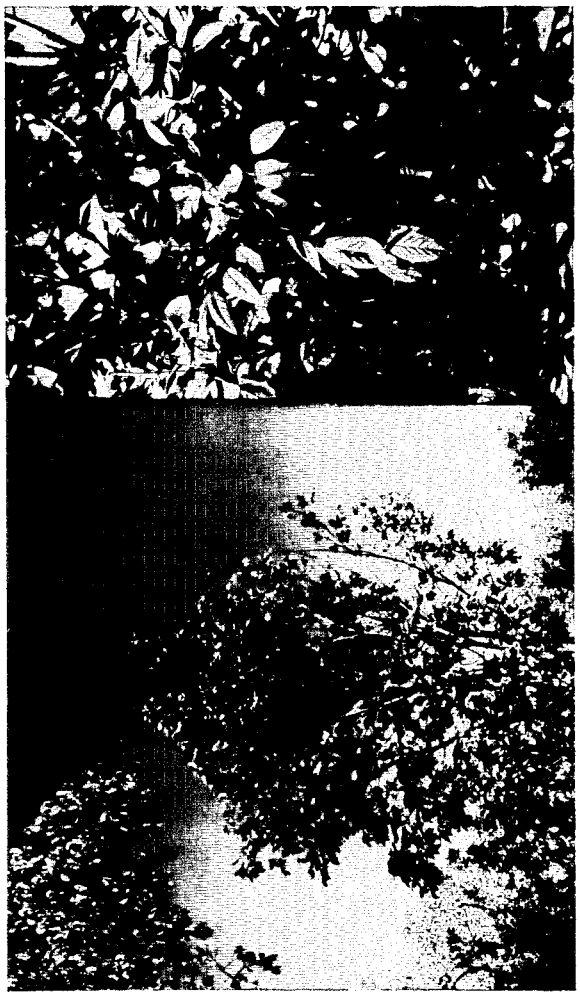
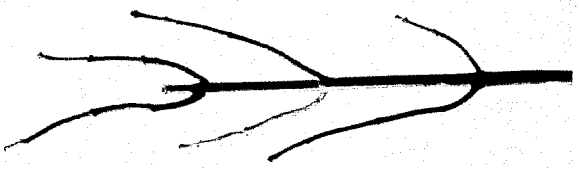
Inventor.
Evert Asjes, Jr.
By: Robbins & Robb
Attorneys.

United States Patent Office

Plant Pat. 2,678
Patented Oct. 11, 1966

2,678
ASH TREE

Evert Asjes, Jr., 116th and Blue River Road,
Kansas City, Mo.

Filed Feb. 23, 1965, Ser. No. 434,726
1 Claim. (Cl. Plt.—51)

The present invention relates to a new and distinct variety of ash tree of the white ash class, which was discovered by me in my nursery at Kansas City, Missouri, as a newly found seedling of an unnamed variety of the species botanically known as *Fraxinus americana.*

Both green and white ash varieties heretofore known are noted for their crooked and ungainly habit of growth, as well as their narrow and weak crotching, and considerable variation of the form of the tree. Generally, both of these types of ash trees have poor fall colors and shed their foliage early. Some European types lack hardiness and are highly susceptible to borers. My new variety of ash tree, which is the subject hereof, has none of these unfavorable characteristics aforementioned and is a distinct improvement over all other varieties of which I am aware.

At the time of my discovery, my attention was attracted to one of several seedlings of unknown parentage which came up on cultivated property in my nursery at Kansas City, Missouri, due to its outstanding fall coloring. Continued observations of this seedling, as well as progeny thereof derived by both grafting and budding the new variety in my nursery at Kansas City, Missouri, confirmed this outstanding feature, as well as other improved features which distinguish my new variety from all others of which I am aware, as evidenced by the following unique combination of characteristics which are outstanding therein:

(1) A fairly rapid, uniform and seedless habit of growth;

(2) A distinctive wide angle crotching habit of the lateral branches;

(3) A distinctive and attractive reddish purple color of the foliage in the fall season, with good foliage retention;

(4) Good winter hardiness;

(5) Good resistance to the usual natural ash diseases and borers; and

6) Ease of propagation by both budding and grafting.

The accompanying drawing shows a typical specimen tree of my new ash variety with the foliage depicted in its fall color, as well as typical foliage specimens on a somewhat enlarged scale to better show the form and color af the foliage, and a specimen of a young tree without foliage, illustrating the wide angle crotching habit of the branches.

The following is a detailed description of my new ash tree with color terminology in accordance with Koster's Color Guide, except where general color terms of ordinary dictionary significance are obvious:

Parentage: A seedling of an unnamed variety of the species botanically known as *Fraxinus americana.*

Class: White ash.

Propagation: Holds its distinguishing characteristics through succeeding propagations by both budding and grafting.

Locality where grown and observed: Kansas City, Missouri.

Tree: Medium size; spreading; dense; hardy.

*Trunk.*—Stocky.

*Branches.*—Stocky. Color—dark gray.

*Twigs.*—Strong (not willowy). Color — grayish green and glabrous. Terminal buds—ovoid; obtuse; covered with from 4 to 6 brown scales. Lateral buds—same as terminal buds, but smaller.

Foliage:

*Leaves.*—Compound of 6 or 7 leaflets; from 6 to 10 inches long.

*Leaflets.*—Length—from 3 to 5 inches. Width—from 1 to 1½ inches. Shape—ovate; rounded at base; slightly dentate at apex. Thickness—medium. Margin — smooth edge. Color — upper side usually rich dark green corresponding to near Taxus Green, Plate 81, with under side glaucous and lighter silvery green, and leaves becoming in the fall a reddish purple, corresponding to near French Purple, Plate 42.

*Rachis.*—Glabrous.

*Petioles.*—Quite short.

*Glands.*—None.

*Stipules.*—None.

*Leaf scars.*—Semi-orbicular and notched at top, with bundle scars in U-shaped arrangement.

Flower buds: Color—Rusty brown.

Flowers:

*Form.*—Flowers comprise small tufts of four-lobed apetalous blossoms which bloom about 10 days before leaves appear.

*Color.*—Reddish.

I claim:

A new and distinct variety of ash tree, substantially as herein shown and described, characterized particularly as to novelty by the unique combination of a fairly rapid, uniform and seedless habit of growth, a distinctive wide angle crotching habit of the lateral branches, a distinctive and attractive reddish purple color of the foliage in the fall season, with good foliage retention, good winter hardiness, good resistance to the usual natural ash disease and borers, and ease of propagation by both budding and grafting.

References Cited by the Examiner

Trees for American Gardens, Donald Wyman, 1951, The Macmillan Co., p. 183.

Manual of Cultivated Trees and Shrubs, Alfred Rehder, 1960, The Macmillan Co., p. 770.

ABRAHAM G. STONE, *Primary Examiner.*

R. E. BAGWILL, *Assistant Examiner.*